(12) United States Patent
Madson

(10) Patent No.: US 9,488,653 B2
(45) Date of Patent: Nov. 8, 2016

(54) SYSTEM AND METHOD OF NON-REDUCTIVE β-ELIMINATION ISOLATION AND ANALYSIS

(71) Applicant: Michael A. Madson, Ames, IA (US)

(72) Inventor: Michael A. Madson, Ames, IA (US)

( * ) Notice: Subject to any disclaimer, the term of this patent is extended or adjusted under 35 U.S.C. 154(b) by 0 days.

(21) Appl. No.: 14/657,352

(22) Filed: Mar. 13, 2015

(65) Prior Publication Data

US 2016/0266122 A1    Sep. 15, 2016

(51) Int. Cl.
G01N 33/574 (2006.01)
G01N 33/53 (2006.01)

(52) U.S. Cl.
CPC ......... *G01N 33/574* (2013.01); *G01N 2400/00* (2013.01); *G01N 2500/20* (2013.01); *G01N 2560/00* (2013.01)

(58) Field of Classification Search
CPC .... G01N 33/574; G01N 33/53; G01N 33/50; G01N 33/48; G01N 2400/00; G01N 2500/20; G01N 2500/00; G01N 2560/00; G01N 33/00
USPC ...................................... 436/87, 86
See application file for complete search history.

(56) References Cited

U.S. PATENT DOCUMENTS

| 8,685,355 B2 | 4/2014 | Madson |
| 2007/0105179 A1 | 5/2007 | Madson |
| 2013/0053602 A1 | 2/2013 | Madson |

OTHER PUBLICATIONS

Soderlund, Robert, Release and analysis of O- and N- linked oligosaccharide from glycoproteins, Uppsala University School of Engineering, Molecular Biotechnology Programme, Examensarbete, Jan. 2008, pp. 1-29.*
STN Search Report obtained on Jun. 21, 2016 from STIC Services at the USPTO, pp. 1-38.*
Madson, M.A.; Christus, J., Structural Characterization of an Unknown Di-phosphorylated Bovine Submaxillary Mucin O-linked Oligosaccharide, 247th ACS meeting, Mar. 16-20, 2014, Dallas, TX.
Christus, J; Madson, M.A.; Simple Method for the Non-reductive β-elimination of O-linked Oligosaccharides of Glycoproteins, 245th ACS meeting, Apr. 7-11, 2013, New Orleans LA.
Halima, A.; Brinkmalmb, G.; Ruetschia,U.; Westman-Brinkmalmb, A.; Porteliusb, E.; Zetterbergb, H.; Blennowb, K.; Larsona, G.; Nilssona, J.; Site-specific Characterization of Threonine, Serine, and Tyrosine Glycosylations of Amyloid Precursor Protein/Amyloid β-Peptides in Human Cerebrospinal Fluid, Proceedings of the National Academy of Sciences of the United States of America, Jul. 19, 2011, pp. 11848-11853, vol. 108 (29).
Madson, M.A.; Christus, J.; MS Method to Discern Phosphate Versus Sulfate Esters of Carbohydrates, 246th ACS meeting, Sep. 8-12, 2013, Indianapolis IN.
Christus, J.; Madson, M.A.; Structural Identification of an Unknown Trisaccharide in Bovine Milk, 243rd ACS meeting, Mar. 2012, San Diego, CA.
Tsuiki, S.; Hashimoto, Y.; Pigman, W.; Comparison of Procedures for the Isolation of Bovine Submaxillary Mucin, The Journal of Biological Chemistry, Jan. 26, 1961, pp. 2172-2178, vol. 236, No. 8.
Madson, M.; Rao, S.; Avdalovich, N.; Pohl, C.; Simple Procedure for the Isolation of N- and O-linked Oligosaccharides from Glycoproteins Glycobiology, Nov. 2005, Boston, MA.
Mechref, Y.; Novotny, M.; Structural Studies of Gycoconjugates at High Sensitivity. Chem. Rev. 102 (2) 321-370 2002.
Takako, Yoshida-Moriguchi, Liping Yu, Stephanie H. Stalnaker, Sarah Davis, Stefan Kunz, Michael Madson, Michael B. A. Oldstone, Harry Schachter, Lance Wells, Kevin P. Campbell; O-Mannosyl PhosPhosphorylation of Alpha-Dystroglycan Is Required for Laminin Binding; Science; Jan. 1, 2010; pp. 88-92; vol. 327; www.sciencemag.org.
Patel, T. P. et al., "Release of Oligosaccharides from Glycoproteins by Hydrazinolysis", Methods in Enzymology, vol. 230, (2) pp. 57-66, 1994.

* cited by examiner

*Primary Examiner* — Christine T Mui
(74) *Attorney, Agent, or Firm* — Zarley Law Firm, P.L.C.

(57) ABSTRACT

A laboratory method and system used to isolate and analyze O-linked oligosaccharides from glycoproteins that uses non-reductive β-elimination (NBRE). The method including the step of providing a predetermined amount of solution and then passing it through an ion exchange resin. The method further includes collecting a second solution off of the ion exchange resin and adding a predetermined amount of sodium hydroxide to form a third solution. The third solution is allowed to stand for a set amount of time at a particular temperature. The third solution is then washed through an ion exchange cartridge in the ammonium form. The collected fourth solution is evaporated and pushed through a sodium form resin prior to being analyzed for its composition.

18 Claims, 4 Drawing Sheets

SYSTEM AND METHOD OF NON-REDUCTIVE β-ELIMINATION ISOLATION AND ANALYSIS

BACKGROUND OF THE INVENTION

This invention relates to a method and system of isolating and analyzing a compound. More specifically, this invention relates to a laboratory method and system that can be used in order to isolate and analyze O-linked oligosaccharides from glycoproteins that uses non-reductive β-elimination (NBRE).

Cancer is a disease that affects millions of families and individuals every year. As a result scientists are in a continuous search for substances that are effective in promoting anti-cancer activity, whether the substances prevent the onset of cancer or alternatively slow down or stop the growth of cancer.

In this pursuit, glycoproteins and their associated saccharides have been a source of tremendous research. Many obstacles arise when isolating the saccharides from glycoproteins that in turn limits the understanding the saccharides' anti-cancer activities. Current methods require the use of reductive methods that are both costly and stifle the level of research as current methods and systems are not as sensitive or stable. Additionally, current methods and systems prevent some forms of analysis that are inhibited due to the reductive measures taken during the method. Therefore, a need in the art exists to address these deficiencies.

Therefore, a primary object of the invention is to provide a method and system that improves upon the state of the art.

Another object of the invention is to provide a method and system that uses fewer chemicals.

Yet another object of the invention is to provide a method and system that uses non-reductive β-elimination.

Another object of the invention is to provide a method and system that increases the sensitivity in analyzing oligosaccharides of glycoproteins.

Yet another object of the invention is to provide a method and system that increases the stability in analyzing oligosaccharides of glycoproteins.

Another object of the invention is to provide a method and system that facilitates the analysis of O-linked oligosaccharides.

Yet another object of the invention is to provide a method and system that is low cost.

Another object of the invention is to provide a method and system that is easy to use.

These and other objects, features, or advantages of the invention will become apparent from the specification, drawings, and claims.

BRIEF SUMMARY OF THE INVENTION

A laboratory method and system used to isolate and analyze O-linked oligosaccharides from glycoproteins that use non-reductive β-elimination (NBRE). The method including the step of providing a predetermined amount of solution and then passing it through an ion exchange resin. The method further includes collecting a second solution off of the ion exchange resin and adding a predetermined amount of sodium hydroxide to form a third solution. The third solution is allowed to stand for a set amount of time at a particular temperature. The third solution is then washed through an ion exchange cartridge in the ammonium form. The collected fourth solution is evaporated and pushed through a sodium form resin prior to being analyzed for its composition.

DETAILED DESCRIPTION OF THE PREFERRED EMBODIMENT

Figure 1:
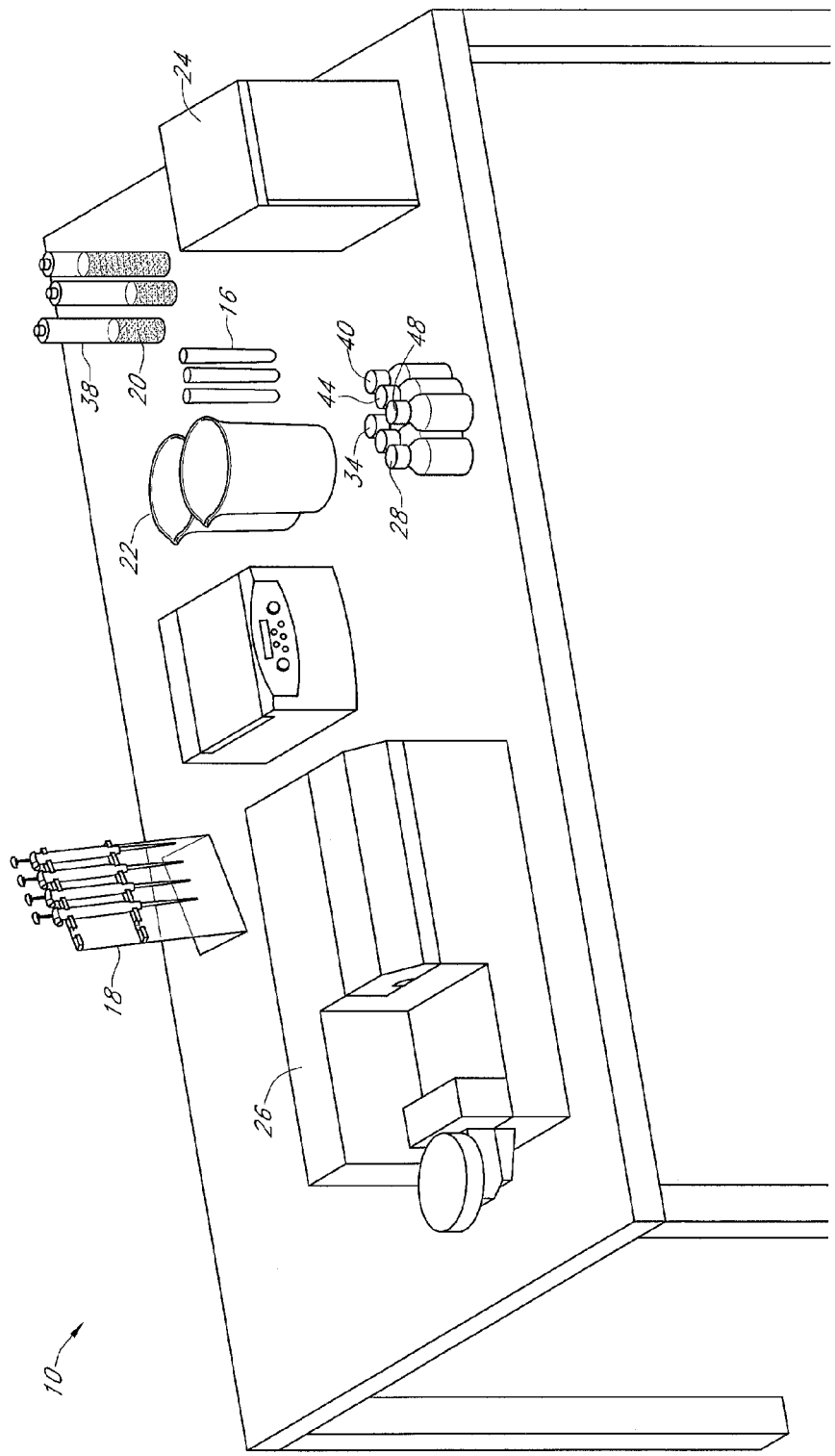
FIG. 1 is a perspective view of the system of non-reductive β-elimination isolation and analysis.
Figure 2:
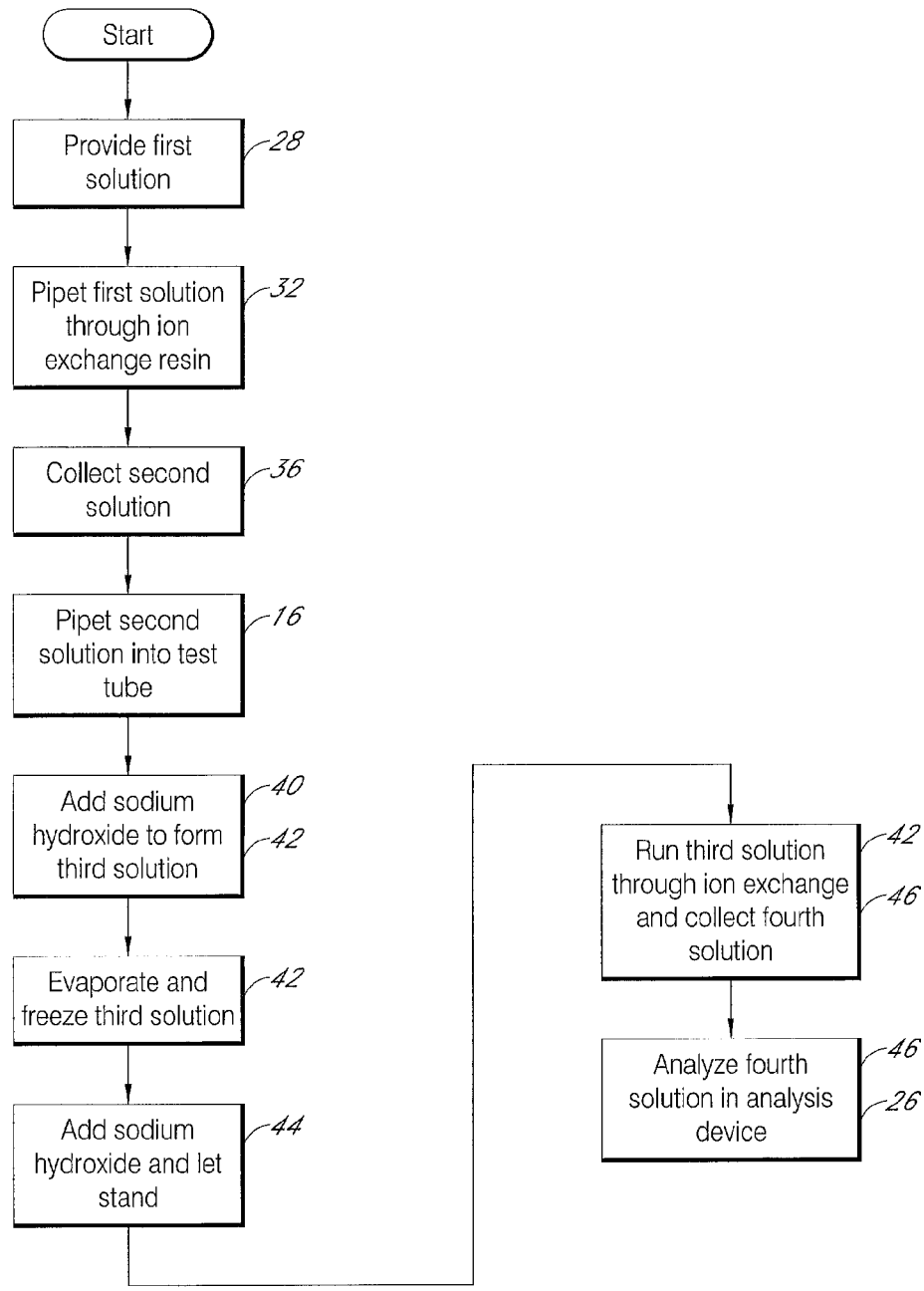
FIG. 2 is a diagram of the system of non-reductive β-elimination isolation and analysis.
Figure 3:
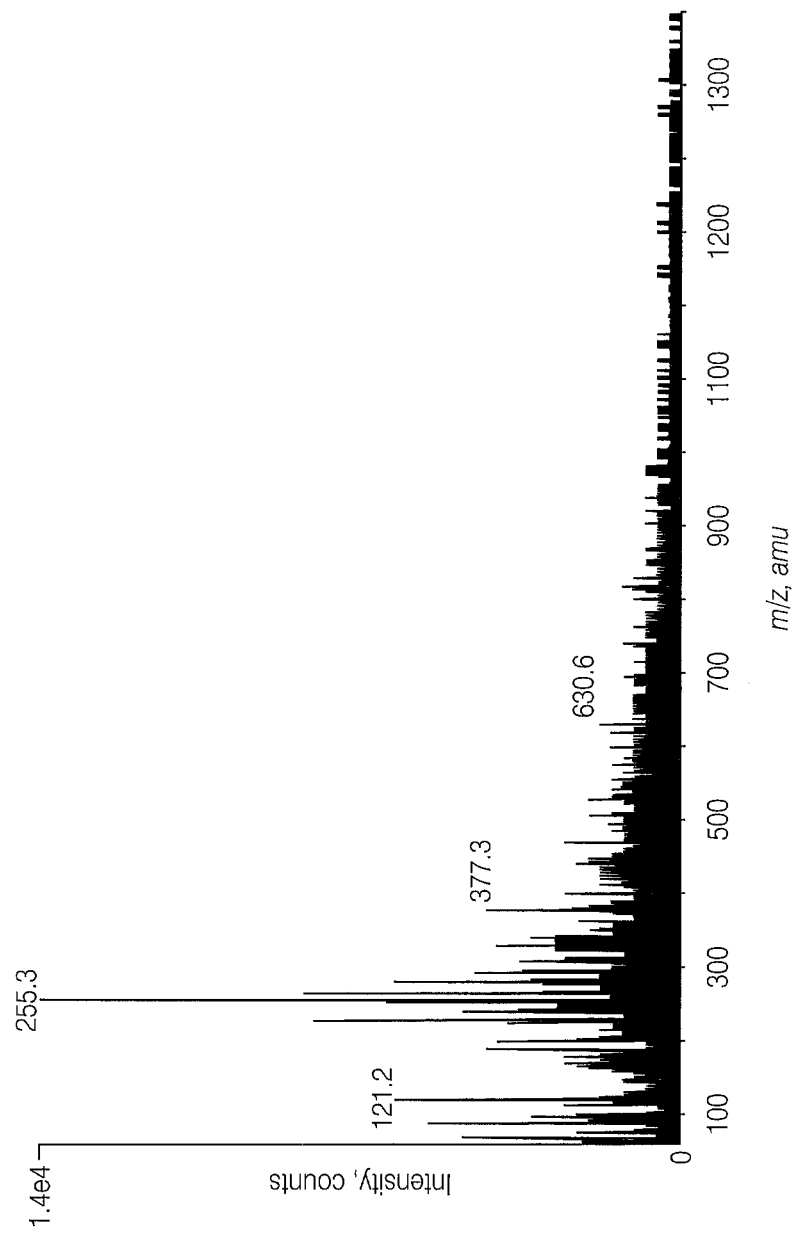
FIG. 3 is a mass spectrum of a glycoprotein solution obtained using non-reductive β-elimination isolation and analysis.

Referring to the figures, the figures show a non-reductive β-elimination (NBRE) system 10 utilized in order to isolate O-linked saccharides. The system 10 includes a test tube 16, a plurality of pipets 18, ion exchange cartridges 20 including one in the ammonium form and one in the sodium form, and a plurality of beakers 22. In addition, the system 10 can include a freezer 24 and one or more analysis devices 26, such as a mass spectrometer (MS) or a high performance anion exchange chromatographer with pulse amperometric detection (HPAEC-PAD).

The NBRE method used to isolate and analyze saccharides from a glycoprotein using the system 10 is to pipet a predetermined amount of a first solution 28 through an ion exchange resin 38, which in one embodiment is in the ammonium form. In one embodiment the first solution 28 is a glycoprotein solution. The resulting second solution 26 is then placed in the freezer 24 until thawed for further analysis. Thawing can be accomplished by placing the first solution 28 in a beaker 22 filled with water 34.

As analysis moves forward, the second solution 26 is thawed if necessary. Then, a predetermined amount of sodium hydroxide (NaOH) 40 is added to the test tube 16, which in one embodiment has a pH of 11.4. No sodium borohydride ($NaBH_4$) is added as this would result in a reductive process. In an illustrative embodiment, 1.0 mL of sodium hydroxide 40 is added to the test tube 16 that contains approximately 0.2 mL of the second solution 36. In one embodiment the sodium hydroxide 40 has a pH of 11.4. The sodium hydroxide 40 removes O-linked oligosaccharide from glycoprotein that is bound to the second solution 36 to form a third solution 42.

The third solution 42 is then evaporated. In one embodiment, the third solution 42 is evaporated until approximately 0.2 mL of third solution 42 remains. After evaporation, the third solution 42 is then frozen.

Next, sodium hydroxide (NaOH) 44 is added to the third solution 42. In one exemplary embodiment, 1.0 mL of sodium hydroxide 44 having a pH of 11.4 is added. The third solution 42 is then let to stand for no more than 50 minutes. In an alternative embodiment, the duration is less than 45 minutes. Allowing the third solution 42 to stand for more than 50 minutes results in higher levels of mannose or other carbohydrate 2-epimer rather than the desired glycan. The third solution 42 is let stand at a predetermined temperature, which can be ambient temperature.

After letting the third solution 42 stand for the predetermined amount of time, the third solution 42 is ran through an exchange cartridge 20, which in one embodiment is an ammonium ion cation exchange cartridge. The third solution 42 is washed with water 34. The resulting washings or fourth solution 46 are then ran through a second exchange cartridge 20, such as a sodium cation exchange cartridge. During the exchange, ammonium ($NH_4^+$) is exchange for sodium ions ($Na^+$).

After the second washing, the fourth solution 46 is evaporated to a predetermined amount and then frozen until later analysis. In one embodiment, the fourth solution 46 is evaporated until approximately 0.2 mL remains.

When analysis is ready to be completed, the fourth solution 46 is analyzed using an analysis device 26 for intact N- and O-linked oligosaccharides. In one illustrative embodiment, the fourth solution 46 is analyzed using a mass spectrometer 26, such as an API 2000 MS. Additionally or alternatively, the fourth solution 46 is analyzed using HPAEC-PAD 26. For example, the HPAEC-PAD can be conducted using 85 mM sodium hydroxide as the eluent on a CarboPac PA 200 column (isocratic).

In an alternative method directed at the analysis of monosaccharide compositions, the above method can be instituted with slight variation. Hydrochloric acid (HCl) 48 is added to the third solution 42 at a predetermined temperature for a predetermined amount of time. For example, 6M hydrochloric acid 48 is added at 100° C. for less than one hour for high acid strength hydrolysis. With low acid strength hydrolysis, 1M hydrochloric acid 48 is added at 100° C. for less than 30 minutes. Monosaccharide component analysis with HPAEC-PAD 26 can be carried out using a CarboPac PA 20 column at 18 mM sodium hydroxide (isocratic).

Figure 4:
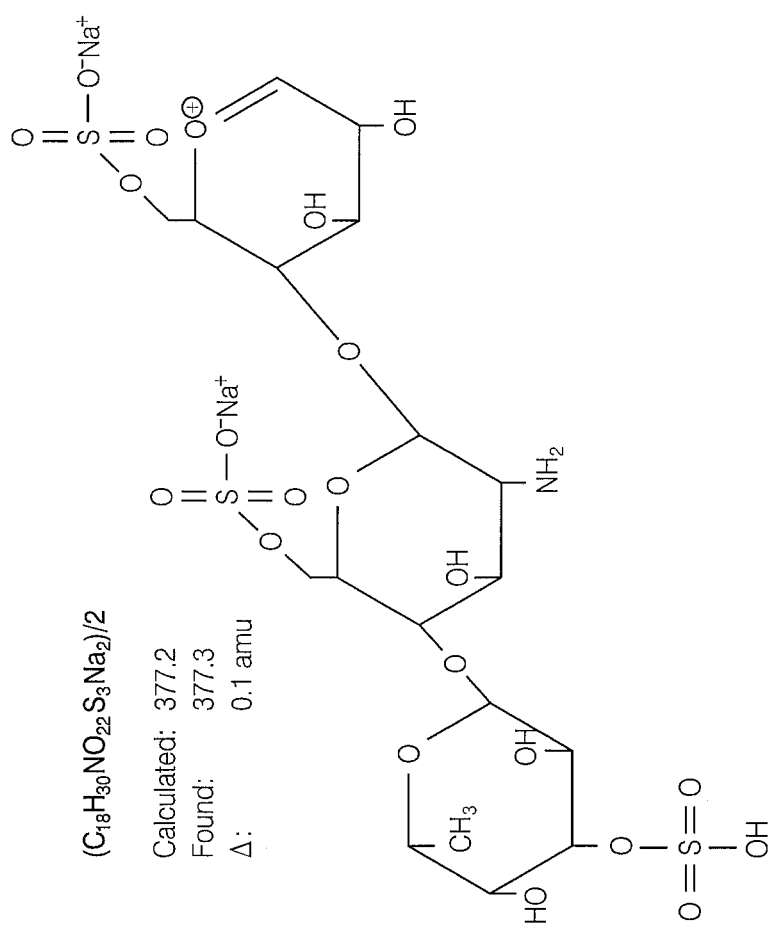
FIG. 4 is a diagram of an ion identified using the non-reductive β-elimination isolation and analysis.

For illustration, shown in FIGS. 4 and 5, the major ion, m/z 377.3, is only present using the system and method of this invention. FIG. 5 shows the loss of ketene common in the mass spectrometry of acetamido sugars such as glcNAc.

Therefore, a non-reductive β-elimination (NBRE) system 10 that uses fewer chemicals, uses a non-reductive β-elimination, increases the sensitivity in analyzing oligosaccharides of glycoproteins, increases the stability in analyzing oligosaccharides of glycoproteins, facilitates the analysis of O-linked oligosaccharides, is low cost, is easy to use, and improves upon the art.

From the above discussion and accompanying figures and claims it will be appreciated that the non-reductive β-elimination (NBRE) system 10, and associated method, offers many advantages over the prior art. It will also be appreciated by those skilled in the art that other modifications could be made without parting from the spirit and scope of the invention and fall within the scope of the claims and are intended to be covered thereby.

What is claimed:

1. A method of non-reductive β-elimination isolation and analysis comprising the steps of:
    providing a predetermined amount of a first solution;
    passing the first solution through an cation exchange resin and collecting a second solution off the cation exchange resin;
    adding a predetermined amount of sodium hydroxide to the second solution to form a third solution;
    letting the third solution stand for a predetermined amount of time;
    washing the third solution through an ion exchange cartridge and collecting a fourth solution off the ion exchange cartridge.

2. The method of claim 1 further comprising the step of analyzing the fourth solution with an analysis device.

3. The method of claim 2 wherein the analysis device is a mass spectrometer.

4. The method of claim 2 wherein the analysis device is high performance anion exchange chromatographer with pulse amperometric detection.

5. The method of claim 1 wherein the predetermined amount of first solution is between 0.1 mL and 1.0 mL.

6. The method of claim 1 wherein the first solution is a glycoprotein solution.

7. The method of claim 1 wherein the amount of sodium hydroxide added to the second solution is 2.0 mL.

8. The method of claim 1 further comprising the step of evaporating the third solution to a predetermined amount.

9. The method of claim 1 wherein 1.0 mL of sodium hydroxide with a pH of 11.4 is added to the third solution.

10. The method of claim 1 wherein the third solution is let to stand no more than 50 minutes.

11. The method of claim 1 wherein the third solution is let to stand no more than 45 minutes.

12. A method of non-reductive β-elimination isolation and analysis comprising the steps of:
    providing a predetermined amount of a first solution;
    passing the first solution through an ion exchange resin and collecting a second solution off the ion exchange resin;
    adding a predetermined amount of sodium hydroxide to the second solution to form a third solution;
    adding a predetermined amount of hydrochloric acid to the third solution;
    letting the third solution stand for a predetermined amount of time at a predetermined temperature.

13. The method of claim 12 wherein 6M hydrochloric acid is added to the third solution.

14. The method of claim 12 wherein 1M hydrochloric acid is added to the third solution.

15. The method of claim 12 wherein the third solution is let stand for no more than one hour.

16. The method of claim 12 wherein the third solution is let stand for no more than 30 minutes.

17. The method of claim 12 wherein the predetermined temperature is 100° C.

18. The method of claim 12 further comprising the step of evaporating the second solution to approximately 0.2 mL.

* * * * *